United States Patent [19]

Unvala

[11] 4,238,830
[45] Dec. 9, 1980

[54] CURVATURE CORRECTION

[75] Inventor: Hoshang A. Unvala, Norwalk, Conn.

[73] Assignee: The Perkin-Elmer Corporation, Norwalk, Conn.

[21] Appl. No.: 62,825

[22] Filed: Aug. 1, 1979

Related U.S. Application Data

[63] Continuation of Ser. No. 685,006, May 10, 1976, abandoned.

[51] Int. Cl.³ .......................... G06F 15/20; G01J 3/42
[52] U.S. Cl. .................................... 364/573; 364/498; 356/325
[58] Field of Search ............... 364/571, 573, 498, 200, 364/900; 250/252, 339

[56] References Cited

U.S. PATENT DOCUMENTS

| | | | |
|---|---|---|---|
| 2,847,899 | 8/1958 | Walsh | 356/95 |
| 3,469,438 | 9/1969 | Gaumer | 73/53 |
| 3,721,813 | 3/1973 | Condon et al. | 340/172 X |
| 3,734,621 | 5/1973 | Moody et al. | 356/95 |
| 3,868,499 | 2/1975 | Aaronson et al. | 250/339 X |
| 3,922,091 | 11/1975 | Suva et al. | 356/95 X |
| 3,927,944 | 12/1975 | Iwahashi et al. | 356/95 X |
| 3,972,617 | 8/1976 | Shibata et al. | 356/95 X |

*Primary Examiner*—Edward J. Wise
*Attorney, Agent, or Firm*—Salvatore A. Giarratana; Francis L. Masselle; Edwin T. Grimes

[57] ABSTRACT

In a dual beam atomic absorption spectrometer having a dedicated microcomputer, improved calibration constants are obtained from either two or three known concentration values by finding a number of constants equal to the number of samples such that when the excess over one of the absorbance of that sample of known concentration multiplied by a second constant is divided into the first constant times the absorbance raised to a power one less than the number of samples or in the case of three samples the difference between that value and a third constant times the absorbance, for each measured sample, the result is equal to the known concentration of the sample.

15 Claims, 17 Drawing Figures

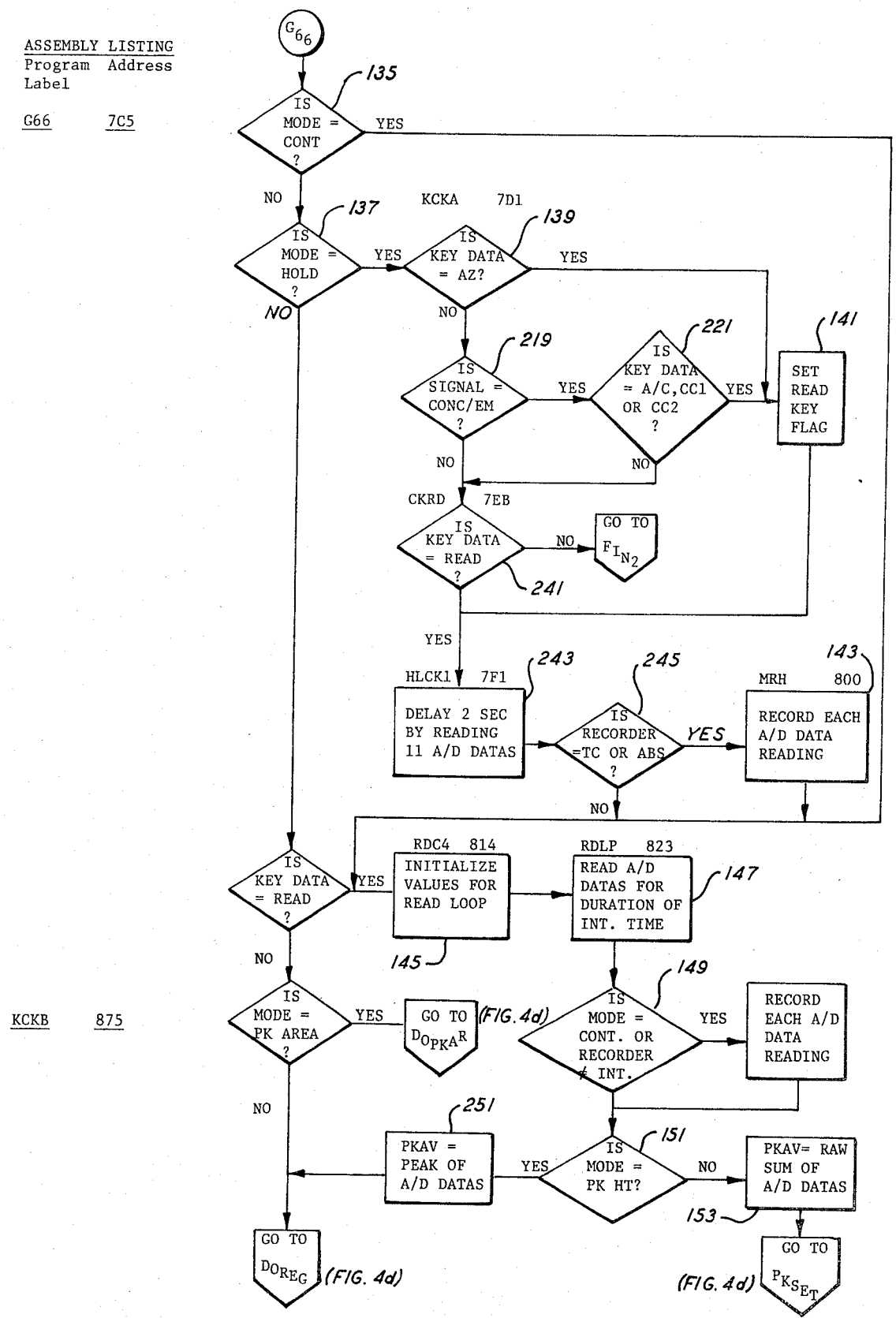

TABLE I

Curve Correction Data for Copper by Flame AA

| Actual Concentration (μg/ml) | Measured Concentration | | | | |
|---|---|---|---|---|---|
| | 2 Standards 2.5 & 25 (10/2/74) | 3 Standards 2.5, 10 & 30 (10/2/74) | 3 Standards 2.5, 10 & 30 (10/23/74) | 3 Standards 2.5, 10 & 30 (10/23/74) | 3 Standards 2.5, 7.5 & 30 (8/20/74) |
| 0 | 0.00 | 0.01 | 0.01 | 0.00 | 0.00 |
| 2.5 | 2.52 | 2.51 | 2.50 | 2.50 | 2.48 |
| 5 | 5.07* | 5.04 | 5.06* | 5.05 | 5.01 |
| 7.5 | 7.50 | 7.47 | 7.49 | 7.49 | 7.47 |
| 10 | 10.01 | 9.98 | 9.97 | 10.01 | 10.03 |
| 12.5 | 12.46 | 12.48 | 12.43 | 12.44 | 12.59 |
| 15 | 15.04 | 14.98 | 14.97 | 15.04 | 15.06 |
| 17.5 | 17.53 | 17.41 | 17.40 | 17.38 | 17.57 |
| 20 | 20.09 | 20.12 | 20.00 | 19.97 | 20.25* |
| 22.5 | 22.49 | 22.58 | 22.21* | 22.36 | 22.57 |
| 25 | 24.93 | 25.10 | 24.71* | 24.81 | 25.14 |
| 27.5 | 27.51 | 27.56 | 27.23 | 27.26 | 27.44 |
| 30 | 30.07 | 30.13 | 29.94 | 29.89 | 29.98 |

*Error more than 1%

FIG. 5

TABLE II

Curve Correction Data for Nickel by Flame AA

| Actual Concentration (μg/ml) | 2 Standards 5 & 15 (10/23/75) | 2 Standards 7.5 & 20 (10/23/75) | 2 Standards 5 & 15 | 2 Standards 5 & 15 | 3 Standards 5, 15 & 30 (10/23/75) | 3 Standards 5, 15 & 30 |
|---|---|---|---|---|---|---|
| 0 | 0.00 | 0.01 | 0.00 | 0.03 | 0.00 | 0.02 |
| 2.5 | 2.47* | 2.45* | 2.48 | 2.51 | 2.47* | 2.51 |
| 5 | 5.00 | 4.96 | 4.98 | 5.04 | 4.99 | 5.02 |
| 7.5 | 7.57 | 7.47 | 7.47 | 7.53 | 7.44 | 7.50 |
| 10 | 10.08 | 10.10 | 10.02 | 10.09 | 9.91 | 10.07 |
| 12.5 | 12.54 | 12.54 | 12.52 | 12.57 | 12.42 | 12.55 |
| 15 | 15.03 | 15.04 | 15.06 | 15.03 | 14.94 | 15.11 |
| 17.5 |  | 17.60 |  |  | 17.39 | 17.50 |
| 20 |  | 20.08 |  |  | 19.87 | 19.99 |
| 22.5 |  |  |  |  | 22.33 | 22.41 |
| 25 |  |  |  |  | 24.81 | 24.86 |
| 27.5 |  |  |  |  | 27.37 | 27.24 |
| 30 |  |  |  |  | 29.91 | 29.95 |

*Error more than 1%

FIG. 6

TABLE III

Curve Correction Data for Cobalt by Flame AA

|  | Measured Concentration | |
| --- | --- | --- |
| Actual Concentration ($\mu$g/ml) | 3 Standards 2.5, 15 & 30 | 3 Standards 2.5, 15 & 30 |
| 0 | −0.02 | 0.01 |
| 2.5 | 2.50 | 2.53* |
| 5 | 5.01 | 5.01 |
| 7.5 | 7.47 | 7.45 |
| 10 | 9.94 | 9.94 |
| 12.5 | 12.53 | 12.43 |
| 15 | 15.08 | 15.11 |
| 17.5 | 17.54 | 17.54 |
| 20 | 20.28* | 20.13 |
| 22.5 | 22.73 | 22.70 |
| 25 | 25.18 | 25.09 |
| 27.5 | 27.65 | 27.67 |
| 30 | 30.08 | --- |

*Error more than 1%

FIG. 7

TABLE IV

Curve Correction Data for Sodium by Flame Emission

|  | Measured Concentration | | |
| --- | --- | --- | --- |
| Actual Concentration ($\mu$g/ml) | 3 Standards 2.5, 10 & 20 | 3 Standards 5, 12.5 & 27.5 | 3 Standards 2.5, 10 & 20 |
| 0 | 0.00 | 0.00 | 0.00 |
| 2.5 | 2.50 | 2.44* | 2.51 |
| 5 | 5.08* | 4.99 | 5.07* |
| 7.5 | 7.56 | 7.38* | 7.53 |
| 10 | 10.08 | 9.92 | 9.99 |
| 12.5 | 12.58 | 12.44 | 12.49 |
| 15 | 15.04 | 15.00 | 14.96 |
| 17.5 | 17.57 | 17.56 | 17.42 |
| 20 | 19.89 | 19.45* | 20.00 |
| 22.5 | 22.63 | 22.51 | 22.43 |
| 25 | 25.00 | 25.12 | 24.74* |
| 27.5 | 27.51 | 27.81* | 27.45 |
| 30 | --- | --- | --- |

*Error more than 1%

FIG. 8

TABLE V

Curve Correction Data for Copper

| Concentration (μg/ml) | Absorbance | 2 Standards 6 & 30 | 2 Standards 10 & 30 | 3 Standards 4, 14 & 30 | 3 Standards 6, 16 & 30 |
|---|---|---|---|---|---|
| 0 | 0.002 | 0.01 | 0.00 | 0.01 | 0.00 |
| 2 | 0.111 | 2.00 | 1.98 | 2.00 | 2.01 |
| 4 | 0.216 | 4.01 | 3.98 | 3.97 | 4.02 |
| 6 | 0.315 | 6.00 | 5.97 | 5.99 | 6.02 |
| 8 | 0.413 | 8.02 | 7.98 | 7.95 | 8.00 |
| 10 | 0.505 | 10.04 | 9.98 | 9.99 | 9.96 |
| 12 | 0.595 | 12.10 | 11.98 | 12.05 | 12.04 |
| 14 | 0.681 | 14.10 | 14.08 | 14.07 | 14.01 |
| 16 | 0.763 | 16.12 | 15.97 | 16.01 | 15.98 |
| 18 | 0.843 | 18.20* | 18.06 | 18.09 | 18.00 |
| 20 | 0.921 | 20.17 | 20.20 | 19.99 | 20.05 |
| 22 | 0.993 | 22.18 | 22.17 | 22.08 | 22.00 |
| 24 | 1.063 | 24.07 | 23.97 | 23.96 | 24.00 |
| 26 | 1.130 | 26.11 | 26.02 | 26.09 | 25.92 |
| 28 | 1.198 | 28.12 | 27.87 | 28.12 | 27.92 |
| 30 | 1.259 | 30.12 | 29.93 | 30.16 | 29.97 |

*Error more than 1%

FIG. 9

TABLE VI

Curve Correction Data for Cobalt

All Calibration With 3 Standards: 4, 12, and 30 µg/ml

| Actual Concentration | Absorbance | Measured Concentration | | | |
|---|---|---|---|---|---|
| | | Trial 1 | Trial 2 | Trial 3 | Average |
| 0 | -0.001 | 0.01 | 0.01 | 0.00 | 0.01 |
| 2 | 0.053 | 2.03* | 2.01 | 2.01 | 2.02 |
| 4 | 0.104 | 4.03 | 4.01 | 4.00 | 4.01 |
| 6 | 0.150 | 6.01 | 5.93* | 5.98 | 5.97 |
| 8 | 0.192 | 7.93 | 7.99 | 7.97 | 7.96 |
| 10 | 0.230 | 9.97 | 9.86* | 9.95 | 9.93 |
| 12 | 0.265 | 12.03 | 11.92 | 11.99 | 11.98 |
| 14 | 0.296 | 14.13 | 14.00 | 14.00 | 14.04 |
| 16 | 0.323 | 15.92 | 15.92 | 15.96 | 15.93 |
| 18 | 0.348 | 18.08 | 18.13 | 17.96 | 18.06 |
| 20 | 0.371 | 20.21* | 19.88 | 19.92 | 20.00 |
| 22 | 0.390 | 22.14 | 22.14 | 22.04 | 22.11 |
| 24 | 0.407 | 24.12 | 24.02 | 24.02 | 24.05 |
| 26 | 0.422 | 26.08 | 26.15 | 26.02 | 26.08 |
| 28 | 0.437 | 28.09 | 27.94 | 28.19 | 28.07 |
| 30 | 0.449 | 29.97 | 29.75 | 30.22 | 29.98 |

*Error more than 1%

FIG. 10

TABLE VII

CURVE CORRECTION DATA FOR LEAD BY FLAMELESS AA

| Actual Concentration (µg/ml) 50 µl Sample | Measured Concentration | | | | | |
|---|---|---|---|---|---|---|
| | Integration 3 Standards 0.1, 0.3 & 0.6 | Peak 3 Standards .1, .3 & .6 | Integration 2 Standards .2 & .6 | Integration 3 Standards .1, .3 & .6 | Peak 3 Standards .1, .3 & .6 |
| 0   | -0.01 | 0.03 | 0.00 | -0.01 | 0.00 |
| 0.1 | 0.10  | 0.10 | 0.09 | 0.10  | 0.09 |
| 0.2 | 0.19  | 0.20 | 0.20 | 0.23  | 0.18 |
| 0.3 | 0.30  | 0.30 | 0.27 | 0.30  | 0.31 |
| 0.4 | 0.40  | 0.39 | 0.38 | 0.40  | 0.39 |
| 0.5 | 0.53  | 0.47 | 0.46 | 0.50  | 0.51 |
| 0.6 | 0.55  | 0.58 | 0.58 | 0.61  | 0.60 |

All data obtained with an atomization temperature of 2300°C

*FIG. 11*

TABLE VIII

CURVE CORRECTION DATA FOR COPPER BY FLAMELESS AA

| Actual Concentration* ($\mu$g/ml) | INTEGRATE | | PEAK READINGS | |
|---|---|---|---|---|
| | Abs-sec | 2 Standards 0.1 & 0.4 | Abs | 2 Standards 0.1 & 0.5 |
| 0 | 0.004 | 0.002 | 0.001 | 0.000 |
| 0.05 | 0.183 | 0.051 | 0.135 | 0.052 |
| 0.1 | 0.361 | 0.104 | 0.241 | 0.102 |
| 0.15 | 0.518 | 0.152 | 0.372 | 0.148 |
| 0.2 | 0.690 | 0.204 | 0.454 | 0.210 |
| 0.25 | 0.863 | 0.261 | 0.585 | 0.256 |
| 0.3 | 1.053 | 0.304 | 0.640 | 0.293 |
| 0.35 | 1.167 | 0.359 | 0.729 | 0.347 |
| 0.4 | 1.291 | 0.417 | 0.853 | 0.405 |
| 0.45 | 1.456 | --- | 0.921 | 0.453 |
| 0.5 | 1.667 | --- | 1.040 | 0.500 |

*20 $\mu$l samples

FIG. 12

CURVATURE CORRECTION

This is a continuation of application Ser. No. 685,006, filed May 10, 1976, now abandoned.

BACKGROUND OF THE INVENTION

This invention relates to spectrophotometers in general and more particularly to a spectrophotometer with improved curvature correction. While the invention is described herein as embodied is a dual channel atomic absorption spectrophotometer, it will be understood that it may also be applied to various other analytical instruments of both the absorption and emission analysis type.

Although the principle of atomic absorption has been known to astronomers for over one hundred and fifty years, its application to chemical analysis only began in 1955. In atomic absorption analysis, the sample is heated to a high temperature, e.g., by burning it in a flame, to break the chemical bond between molecules, freeing individual atoms. In this condition, the atoms can absorb ultraviolet or visible radiation. The wavelength bands which each specific element can absorb are very narrow and are different for every element. The flame used for burning is commonly acetylene with compressed air used as the oxidant. Higher temperatures which are needed for what are known as the "refractory" elements are achieved using nitrous oxide as an oxidant.

If the analyst wishes to determine the concentration of aluminum, for example, he passes the light from a suitable spectral source through the flame. The source is generally a hollow cathode or electrodeless discharge lamp which contains the element of interest, in this case aluminum. A certain portion of the light will be absorbed by free aluminum atoms in the flame, depending on the concentration of aluminum in the sample. The instrument measures the amount of absorption. Modern atomic absorption spectrophotometers can be set to present results directly in concentration values. The analyze extremely small samples, to determine ultra-low concentrations, or to analyze certain solids directly, new sampling devices which augment or replace the flame are available. The most important of these is the graphite furnace or heated graphite atomizer.

As is well known in spectroscopy, the concentration of a radiation absorbing substance is directly proportional to the absorbance A which is defined by the equation $A = \log [I_0/I]$, where $I_0$ is the intensity of the radiation reaching the sample and I is intensity of the same radiation transmitted by the sample. Typically, the quantities $I_0$ and I are determined through the use of a double beam type spectrometer in which one beam passes through the sample and the other beam passes around it. Difficulties are encountered, however, in making these measurements and as a result, the relationship between absorbance and concentration deviates from linearity; the deviation is normally referred as curvature and techniques for compensating for this are termed curvature correction, curve straightening or curve compensation.

A discussion of this problem and a solution using analog circuitry is disclosed in U.S. Pat. No. 3,739,164 issued June 12, 1973.

Analog curvature correction systems, although adequate, are difficult to operate requiring numerous settings by the operator or analyst if he is to obtain accurate results. Because each different element exhibits different curvature characteristics and because the curvature changes with changing concentrations, constant adjustment of analog devices is necessary to obtain the desired accuracy of results.

A solution to the problems associated with the use of analog circuitry in such an instrument is proposed in a paper titled "Use of a Small Dedicated Computer in the Design of an Atomic Absorption Spectrophotometer" by T. J. Poulos which was presented at the Pittsburgh Conference on Analytical Chemistry and Applied Spectroscopy, March 6, 1974. In that article, the author points out the manner in which a microprocessor along with appropriate read-only memories [ROMS] and random access memories [RAMS] can be used to construct a microcomputer which can be used to carry out the data processing in an instrument of this nature including the curvature correction. Briefly, the system discloses integrating the detector signal in an analog integrator, sampling and holding the integrated output, converting it in an analog-to-digital converter and providing the output of the converter as the microcomputer data input. The microcomputer then takes the data input and calculates concentration from the equation:

$$C = k_{C1} \log 1 C2 k_{C2} [1t^{t} - {}^k C2]1^t$$

and absorbance as $A = \log 1^t$ where t is the transmittance.

The use of the microcomputer in the instrument offers many advantages as to simplicity and accuracy. However, tests run using the computation scheme proposed in the paper by Poulos using actual measurement data were found to exhibit inaccuracies which are intolerable in some applications. The concentration range covered for good accuracy was found to be small. The use of the scheme in analyzing for cobalt, which exhibits high curvature, produces good results but the results in the determination of copper, which exhibits a fair degree of linearity, were not quite so good. In attempts to handle sodium emission data, there was no success at all. Thus, although the applicability and advantages of using a small dedicated microcomputer in an atomic absorption spectrophotometer has been recognized, instruments developed to date do not exhibit the desired accuracies over the full range of concentrations which must be measured nor are they capable of handling all samples which must be analyzed. In view of this, the need for an improved curvature correction for spectrophotometers which permits operation over wide concentration ranges on a maximmum number of elements, becomes evident.

SUMMARY OF THE INVENTION

The present invention provides a solution to these problems. It is based on a conventional dual beam atomic absorption spectrometer optical system such as disclosed in detail, for example, in U.S. Pat. No. 2,847,899 and briefly disclosed in the aforementioned article by Poulos. As with Poulos, the detector output of the spectrometer is provided as an input to a microcomputer which carries out the necessary curvature correction and computes outputs in terms of either absorbance or concentration. However, the present instrument exhibits improved accuracy over a wide range of concentrations for numerous substances. This is accomplished primarily through the use of an improved calibration and curvature correction.

In the instrument of the present invention, the output of the photomultiplier is coupled to an amplifier and demodulator with the demodulator output coupled to a log converter. As noted above, the relationship between the absorbance and transmitted light intensity is logarithmic. After conversion into an absorbance value through the log converter, the signal is coupled either to an integrator or peak reader. The integrator is used when a flame atomizer and the peak reader when using a graphite furnace. The output of whichever of the integrator and peak reader are being used is then coupled through an analog-to-digital converter into the microprocessor. By performing the log conversion outside the microprocessor, more time is available therein for carrying out the necessary curvature corrections.

In operation, the system is first calibrated. This is done by entering on an associated keyboard the concentrations of three standards to be used. For example, in a cobalt determination, the standards might be 4.00, 12.00 and 30.00 mg/ml to provide a 0 to 30 mg/ml working range. Thereafter, a blank is aspirated and an auto zero button pressed. The instrument automatically takes an integrated reading for the time selected and adjusts that reading as the zero level. In other words, that level will be subtracted from all other measurements taken. Thereafter, the standards are atomized, the instrument integrating over each of them and determining measured values of absorbance. Either two or three standards may be used. From the known concentration data, constants $K_1$ and $K_2$ or constants $K_1$, $K_2$ and $K_3$ are determined using the following equations depending on whether two or three standards are used:

2 standards:
$$CONC = \frac{K_1(ABS_i)}{K_2(ABS_i) - 1}$$
where: $i = 1, 2$, the sample number 3 standards:
$$CONC = \frac{K_1(ABS_i)^2 - K_3(ABS_i)}{K_2(ABS_i) - 1}$$
where: $i = 1, 2, 3$, the sample number The absorbance values (ABS) entered into these equations are, of course the values after being zeroed using the auto zero value. These equations describe the three characteristics of absorption data in that when absorbance is 0, concentration is 0; with absorbance equal to some value $1/K_2$ concentration versus absorbance is a straight line. Once calibration is accomplished, samples are atomized, measurements taken and the determined constants placed into the equations given above to calculate concentration from the absorbance value. As will be seen from the examples given below, extremely accurate results were obtained. It will also be appreciated that flame emission data have similar characteristics and, therefore, the same equations are applicable thereto.

BRIEF DESCRIPTION OF THE DRAWINGS

FIGS. 4a–4f is a flow diagram for the microcomputer shown in FIG. 3; and

FIGS. 5–12 are tabulations of actual curvature correction data obtained using the method and apparatus of the present invention.

DESCRIPTION OF THE PREFERRED EMBODIMENT

Figure 1:
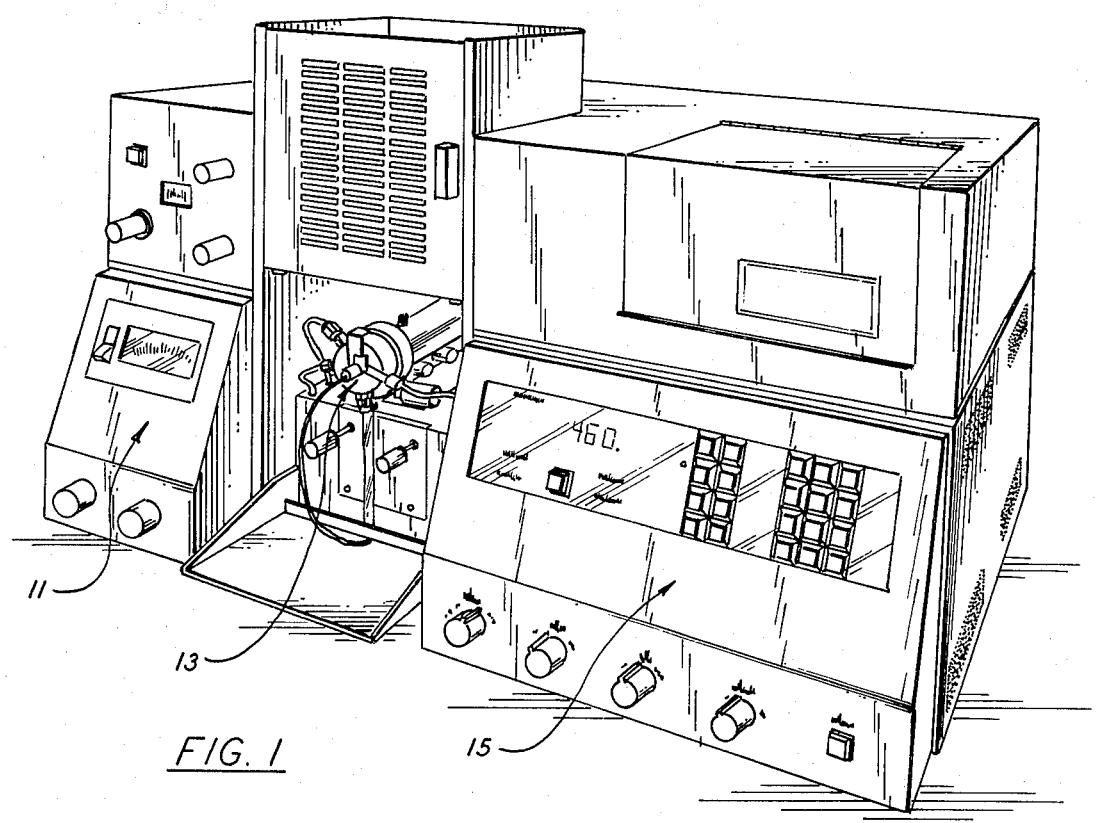
FIG. 1 is a perspective view of an atomic absorption spectrophotometer utilizing the present invention.

FIG. 1 is a perspective elevational view of a complete atomic absorption spectrophotometer embodying the present invention. Such an instrument may be considered as composed of three basic systems: an optical system, including a spectral source such as a hollow cathode or electrodeless discharge lamp and a monochromator; a sampling system which may include a graphite furnace or open flame burner for atomizing the specimen undergoing analysis; and an input/output system including photodetectors and a computation and data display section. In FIG. 1, the only portion of the optical system which is visible from the exterior of the instrument is the control unit 11 for the spectral source; a substantial part of the sampling system is visible and designated by reference numeral 13; and the input and display panel of the input/output system appears at 15 and is shown on a larger scale in FIG. 2. For additional background information regarding atomic absorption spectrophotometers, reference may be had to the prior art including the aforementioned U.S. Pat. Nos. 2,847,899 and 3,469,438.

Figure 2:
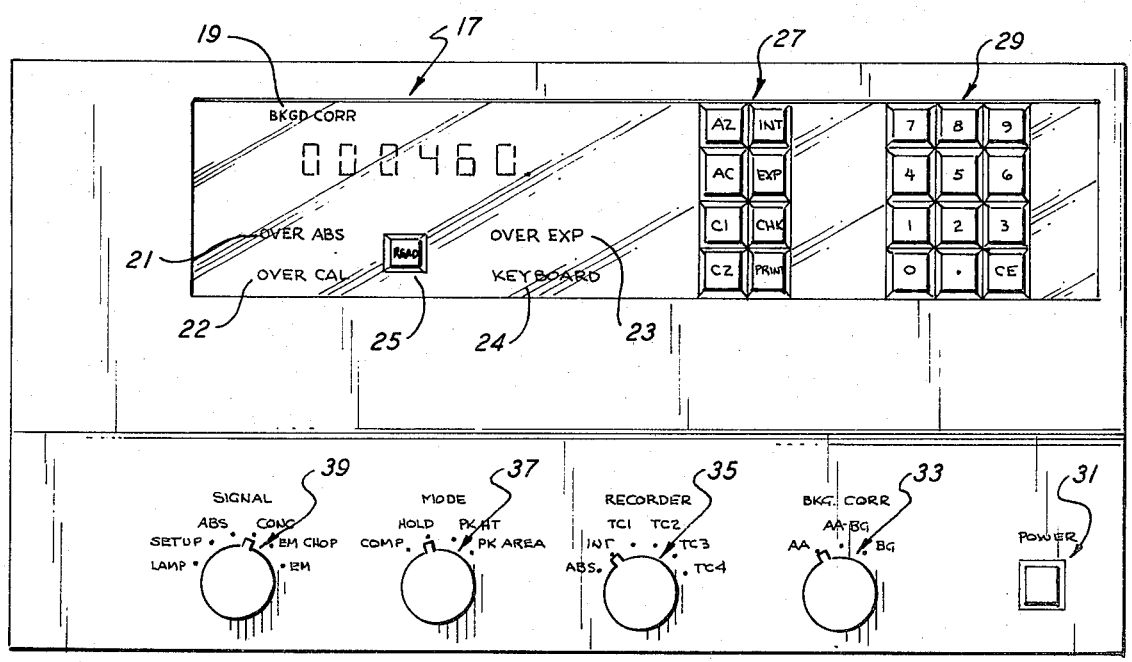
FIG. 2 is a view of the control panel of the spectrophotometer of FIG. 1.

The input and display panel of FIG. 2 includes a digital display 17 and associated therewith a number of lamp displays. In each case, these comprise a legend with a lamp next to it. If the lamp is lit, the function described by the legend is present. Shown are a light display 19 for background correction, a light display 21 for over-absorbance, a light display 22 for over-calibration, a light display 23 for over-exposure and a light display 24 for keyboard. In addition, there is a read key and lamp 25, the lamp located directly above the read key. Next to this section of the panel is a group of function keys 27. These include an auto zero key (AZ), keys labeled A/C, C1 and C3 for entering the sample values, an integrate key (INT), an expanded scale key (EXP), a check key (CHK) and a print key. Next to these are a group of numerical keys 29 for entering numbers along with a decimal point key and a clear entry key (CE). Below this section of the panel is an additional panel which includes a power switch 31 for turning on power, a background correction switch 33, a recorder switch 35, a mode switch 37 and a signal switch 39. The function keys auto zero and A/C, C1 and C3 along with the scale expansion key and the print key have monitor lamps adjacent thereto to indicate that they are in use. The manner in which the various inputs and displays are used will be explained in greater detail below.

Figure 3:
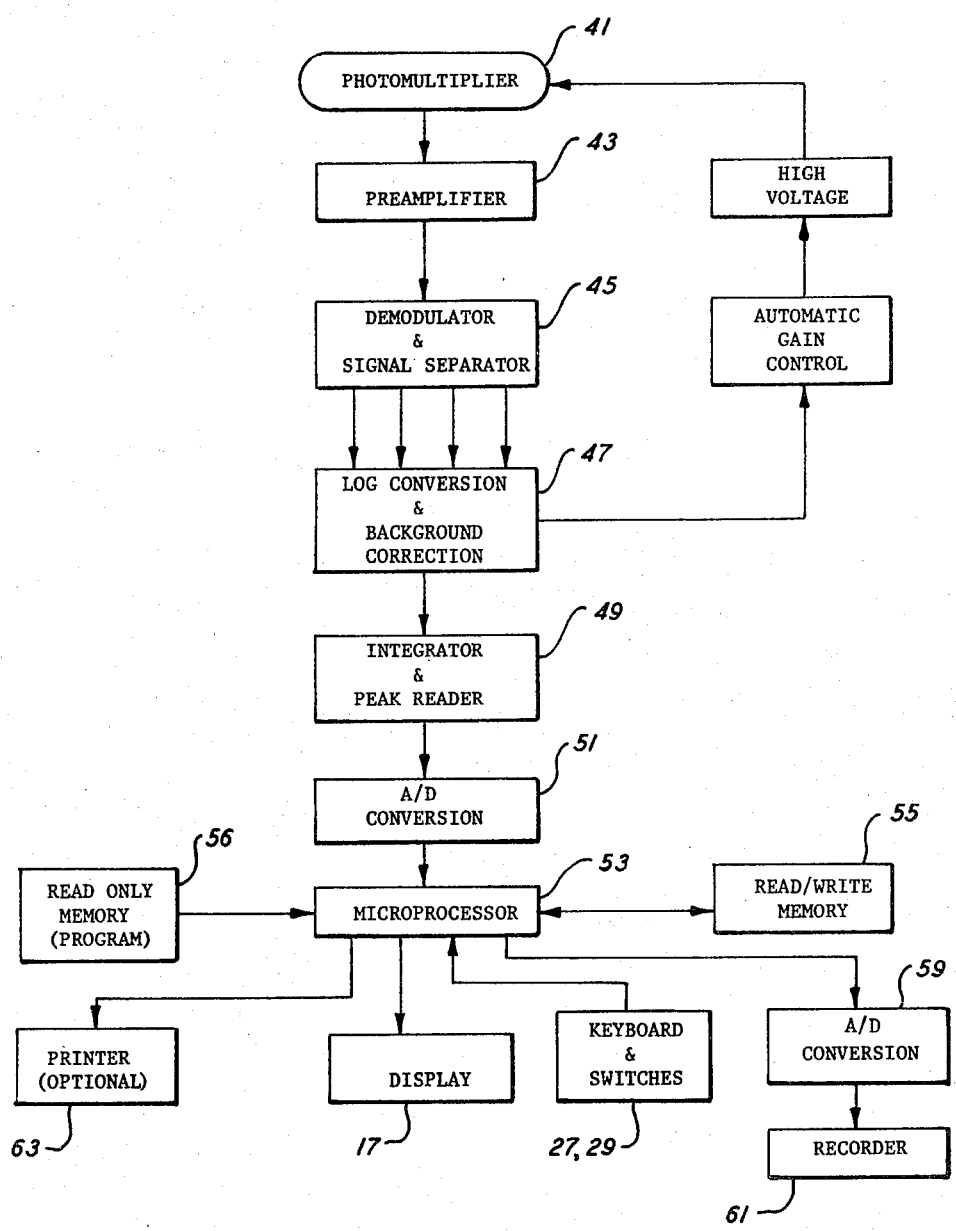
FIG. 3 is a block diagram of the apparatus of the present invention, including the microcomputer.

The basic signal flow in the instrument and microprocessor is illustrated on FIG. 3. From the photomultiplier tube 41 the signal is supplied to a pre-amplifier 43, a demodulator/signal separator 45 and then to a log converter and background corrector 47. This portion of the system is of a design quite similar to that of the aforementioned U.S. Pat. No. 3,739,164. The signal out of the log converter, which will now reflect absorbance, is coupled to an integrator and peak reader 49, the output of which is coupled to analog-to-digital converter 51 the output of which is in turn provided to microprocessor 53.

Microprocessor 53 communicates with a random access memory 55 used for temporary storage and a read only memory 56 used for permanent program storage. It also obtains inputs from the keys 27, 29 and provides an output to the display 17 of FIG. 2. It can also provide an output through a digital-to-analog converter 59 to a recorder 61 and optionally to a printer or teletype device 63. Although any microcomputer can be used, the particular microcomputer employed in the present instrument includes a microprocessor and associated components manufactured by Rockwell International. As is well known, these microprocessors can be equipped with the necessary input/output devices to receive key inputs, A-D inputs, provide display outputs, etc.

A flow diagram for the microcomputer used in the instrument of the present invention along with the portion of the program listing dealing with the specific improvement of the present invention are given below. As is common practice in microcomputers, once a flow diagram is established, a program is written and tested. After the program is determined to be correct for the instrument, either through simulation on a general purpose digital computer or through use of a programmable read only memory storing that program in a test instrument, an assembler program provided by the microcomputer manufacturer is used to convert the program into a series of instructions, contained on data cards, for programming of the read only memories. These cards are prepared by the user and then supplied to the manufacturer who makes the read only memories containing the program using apparatus designed for that purpose. Thus, the read only memories 56 of FIG. 3 will contain a program in accordance with the flow diagrams and program listings given below to permit carrying out all the necessary and desired functions of the spectrophotometer.

Flow diagrams for the instrument are shown on FIGS. 4a-4f. The operation of the instrument will be explained with reference to these flow diagrams and the other figures, particularly FIG. 2.

When starting up the instrument, the power is turned on by operating the switch 31 of FIG. 2. Initially, the signal control is switched to the "Lamp" position and the lamp current set up using the controls in the section 11 of FIG. 1. The signal control 39 is then set to "Set Up" and the wavelength and monochromator slit properly set. The signal control 39 is then set to "CONC" indicating a concentration display. If flame emission measurements are to be made, it is set to "EM Chop". The background correction switch is set to "AA" and the mode control switch to "Hold". In "Hold", readings must be initiated by pressing the read switch 25. The burner gas controls are adjusted and the gas ignited. An integration time is set by entering the desired integration period with the numerical keyboard 29 and pressing the "INT" key.

Figure 4A:
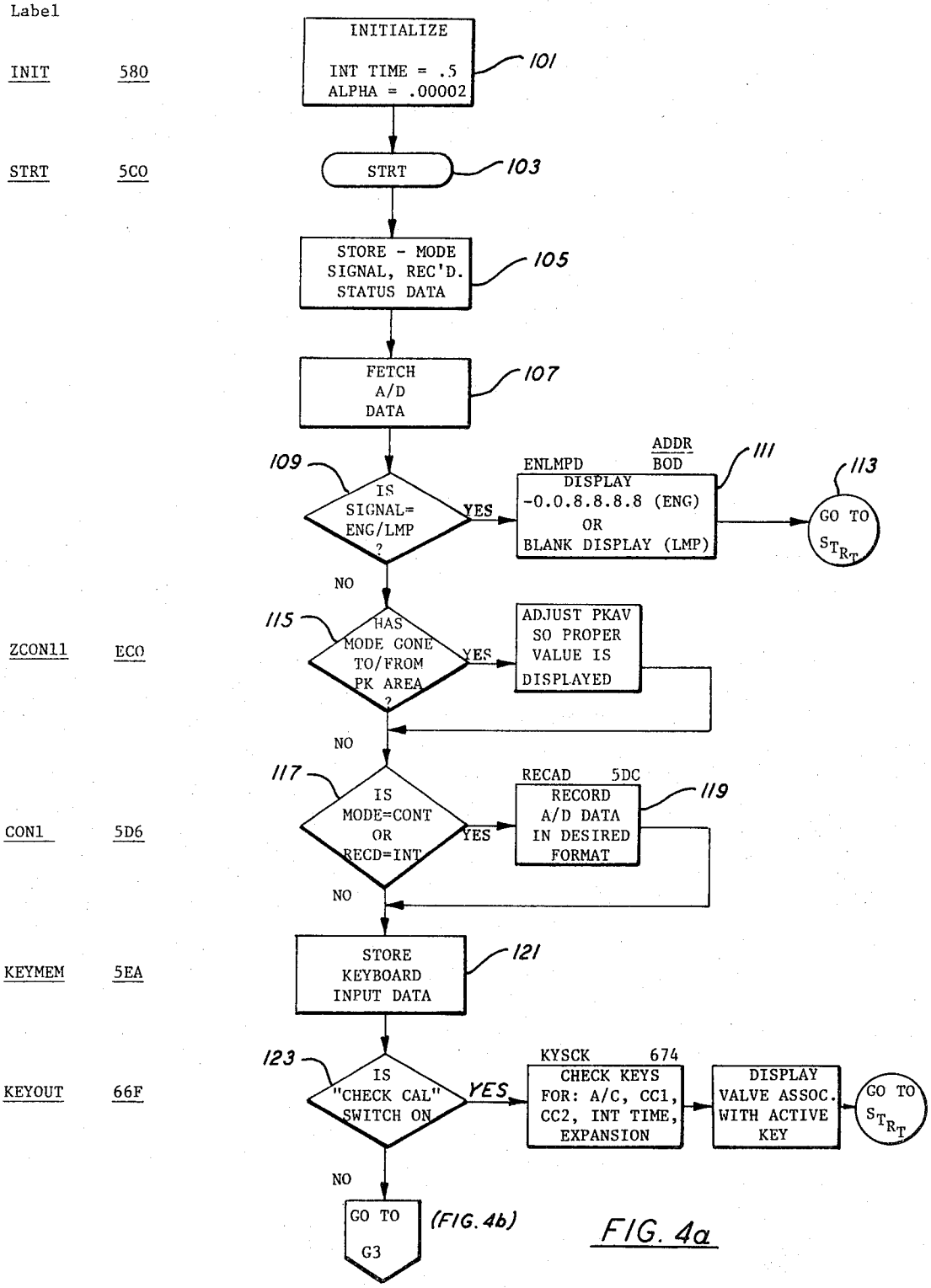
Figure 4B:
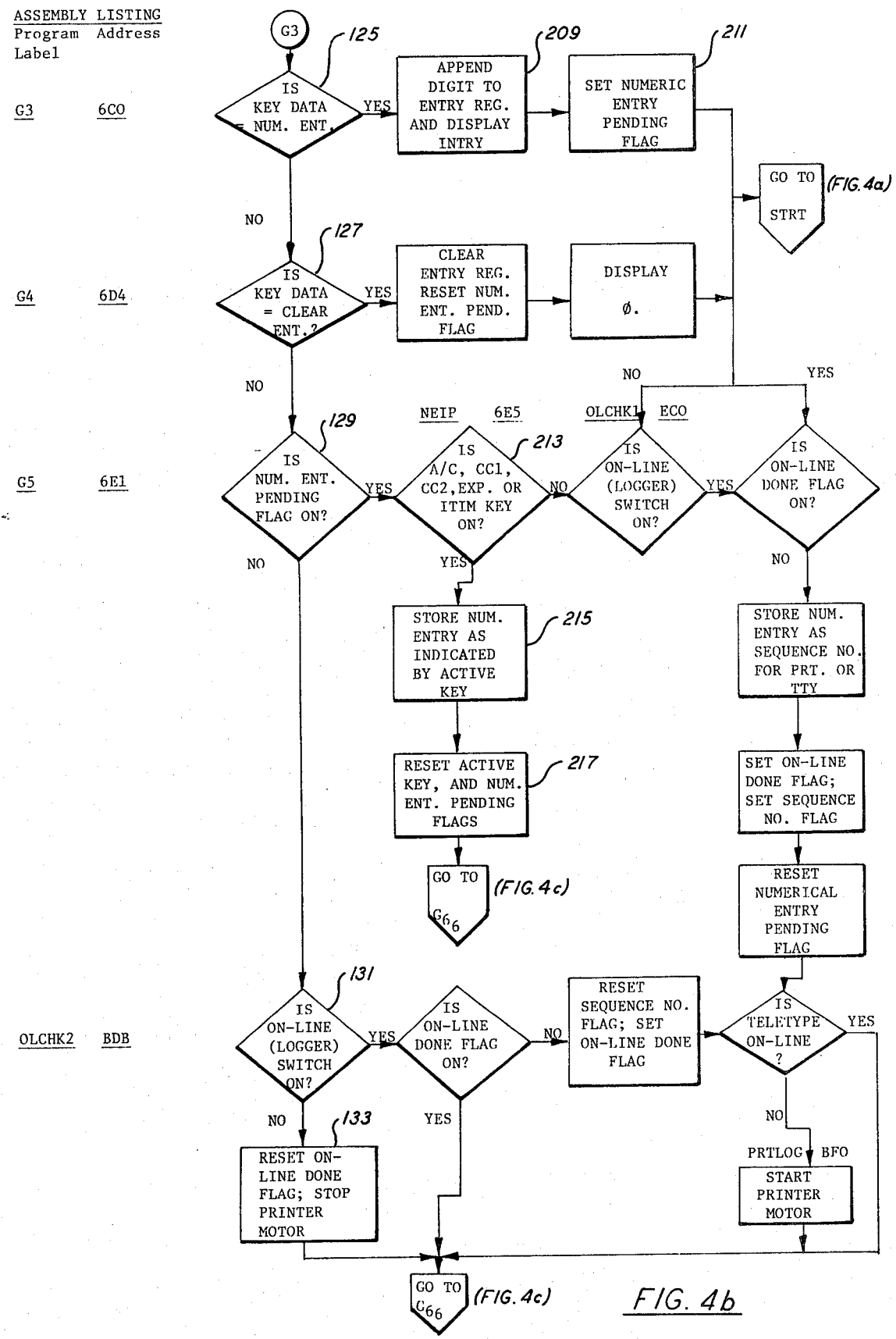

With reference to FIG. 4a, it will be seen that upon turn-on and initialization, the integration time is automatically initialized to 0.5 seconds in block 101. Only if a change is desired need an integration time be entered. Thereafter, the program is started as indicated by block 103. The mode, recorder signal and other data set in are stored in accordance with block 105. The next instruction (107) is to fetch the analog-to-digital data. After the initial set up, a blank solution aspirated and the auto zero key "AZ" of keyboard 27 is pressed. The program, after fetching the analog-to-digital converter data, enters a decision block 109 which asks whether the signal is set either to "ENG" or "Lamp". If the answer is yes, the default test pattern is displayed in accordance with block 111. In either case, this block is exited and as instruction 113 indicates a return to start and the blocks 103, 105, 107, and 109 are gone through again. Thus, during the lamp adjustment, the program will continue in this loop. In the example given above, the control is not set to one of these settings, so the decision block 115 is entered which asks whether or not the mode has gone to or from peak area. Since it has not, the next decision block 117 is entered. Here the question is asked if the mode is equal to CONT or if the recorder is not at INT. Since the answer to this question is yes, the block 119 is entered and the analog-to-digital data is recorded in the desired format.

As noted above, at this time, a blank is being aspirated. Block 121 is then entered causing the keyboard data to be stored. In other words, the indication that auto zero has been pressed is stored. After carrying out this function, the decision block 123 is entered and a check made to see if "CHECK CAL" is on. Since it is not, this portion of the program is exited and it proceeds to G3 on FIG. 4b. From here, an additional decision block 125 is entered where the question is asked whether there is a numerical entry from the keyboard. Since there is not, the decision block 127 is entered where the question is asked whether or not there is a clear entry. Again, there is not, and the decision block 129 determines whether a numerical entry pending flag is on. Such would be the case if one of the keys A/C, CC1 or CC2 were pressed indicating that calibration data was to be entered. Since these have not been pressed, the decision block 131, which asks if the on line (logger) switch is on, is entered. This is a switch coupling to output recording apparatus and it will be presumed for the present that it is not on. Thus, the block 133 will be entered causing a reset of the online done flag and stopping of the printer motor. The program is then instructed to go go G66 on FIG. 4c.

Here, a decision block 135 is entered asking whether mode is CONT. As noted above, mode has been set to HOLD so the answer is "no" and decision block 137 is entered asking if the mode is HOLD. The answer to this question is "yes" so the decision block 139 is entered where the question is asked whether or not the key data is AZ. The answer to this question is "yes" so the block 141 is entered instructing the read key flag to be set. From this block, the block 243 is entered which instructs a 2 second delay by reading 11 A/D data; the program then passes to decision block 245 which asks whether the recorder is TC or ABS; as the answer is "no:, it will pass to block 145 and thence through blocks 147, 149, 151 and 153. It should be noted with reference to FIG. 3, that the integrator 47 integrates over the preset integration time and at the end of that time is reset and its value transferred from the analog-to-digital converter to the microprocessor. This is what is meant by recording each data reading. In other words, a data reading will be recorded each time the integrator is reset.

After exiting block 143, the values are initialized for a reading as instructed by block 147 and the analog-to-digital data read for the duration of the integration time. From this block, a decision block 149 asking whether the mode is CONT or the recorder is not INT is entered. Since the answer to this question is "no", the decision block 151 is entered where the question is asked whether or not the mode is peak height. Since the answer to this question is also "no", the instruction block 153 is entered instructing that the value PKAV be set to the raw sum of the A-D data which were recorded.

Figure 4D:
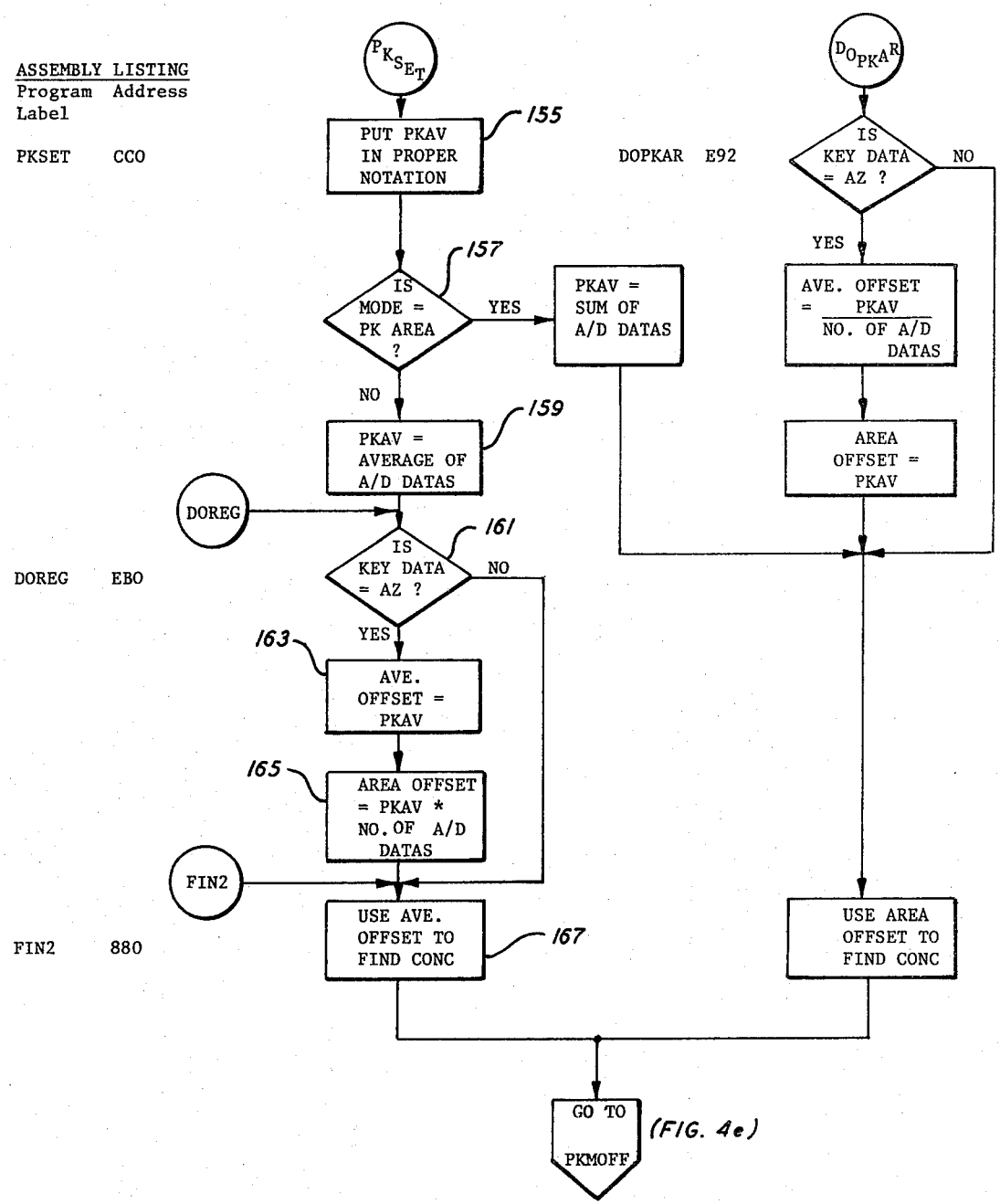

The program then exits to go to FIG. 4d where it enters at PKSET and passes to instruction block 155 which instructs that PKAV be put in the proper notation after which it enters a decision block 157 where the question is asked whether or not the mode is peak area. The answer to this is "no" and the instruction is given that PKAV is the average of A-D data in block 159. A decision block 161 is entered where the question is asked whether or not key data is AZ. The answer to this is "yes" and in block 163, the average offset is set to PKAV. Thereafter, in block 165, the average offset is set equal to PKAV times the number of A-D data. Then the block 167 is entered where the instruction is given to use the average offset to find concentrations.

Figure 4E:
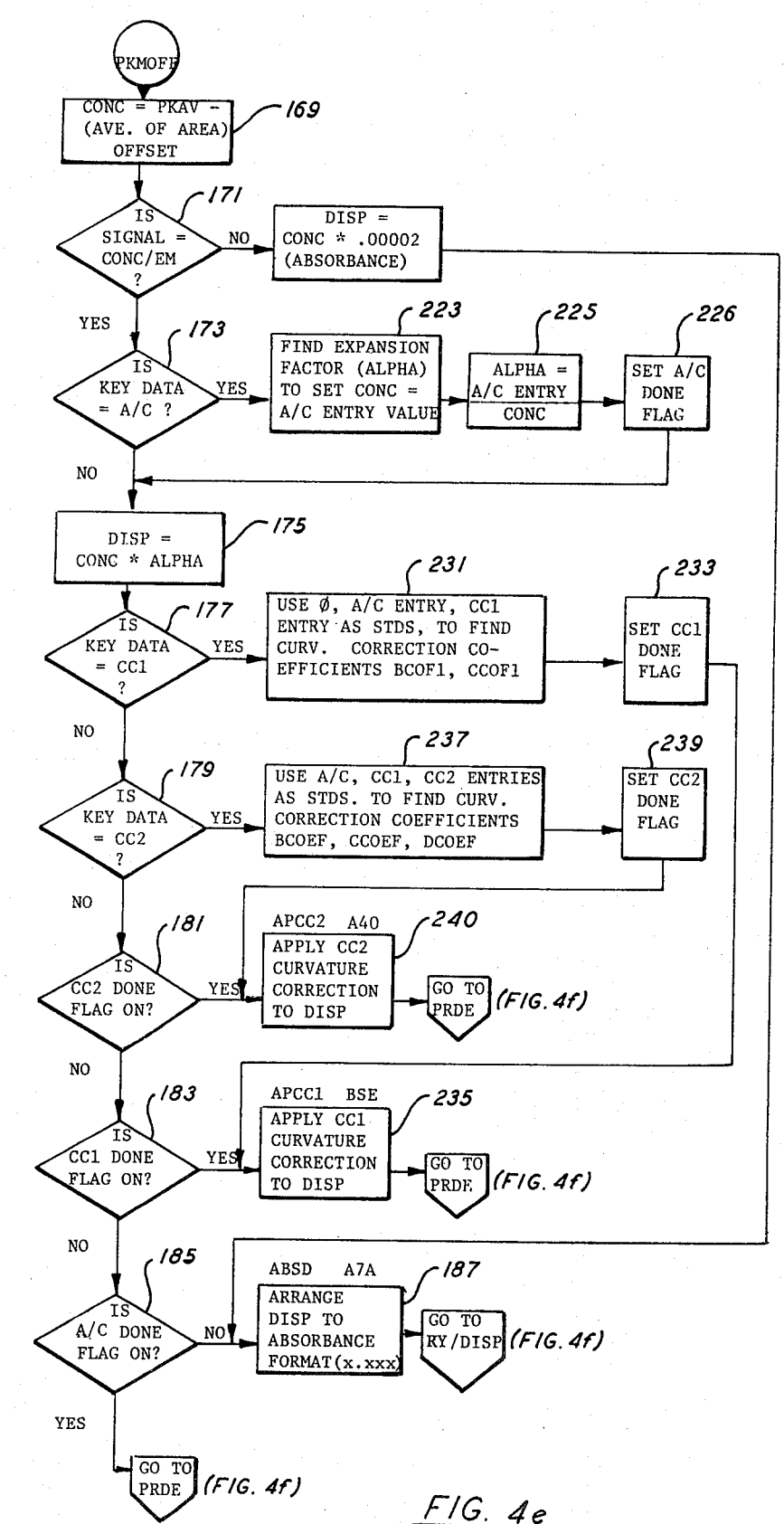

The program then exits to PKMOFF shown on FIG. 4e. Here, the first block indicates that concentration equals PKAV minus average or area offset. Then a decision block 171 is entered asking whether the signal is CONC or EM. Since the signal is CONC, the block 173 is entered where the question is asked whether the key data is A/C. (A/C refers to the entry of only one calibration standard.) Since the answer to this is "no", the block 175 is entered and measured concentration times alpha, which was preset during the initialization, is checked.

The program then passes through decision blocks 177 and 179 which respectively ask whether the key data is CC1 or CC2. CC1 indicates that both switches A/C and CC1 were pressed to enter two standards. CC2 indicates that all three switches, A/C, CC1 and CC2 were pressed to enter three standards.

The program then passes through the decision blocks 181 and 183 where the question is asked whether or not the CC2 done flag is on and the CC1 done flag is on. Since these were not done, the answers will be "no". Decision block 185 then asks whether A/C done flag is on. The answer to this is "no" and the block 187 is entered which indicated that the display is arranged to display absorbance. The program then goes to RYDISP on FIG. 4f. The decision block 189 is entered asking whether the mode is CONT or the read flag is on. The answer to this is "no" and the decision block 191 is entered asking if the key is set for AZ, A/C, CC1 or CC2. The answer to this is "yes" and an instruction given on block 191 to display the DISP value. Then a decision block 195 is entered asking if the on-line logger switch is on. Since this is presumed to be off, the answer is "no" and decision block 197 is entered. Here, the question is asked whether or not the mode is equal to CONT or the recorder not INT. The answer to this is "no" and the question is asked in block 199 if the signal is CONC or EM. The answer to this is "yes" and the question is asked in block 201 whether A/C done flag is on. The answer to this is "no" and the indication given then in block 203 to arrange the DISP value to the absorbance format. Thereafter, the instruction is given in block 205 to record the DISP value and then an instruction in block 207 to RESET the read key flag whereupon the program is directed back to block 103, the start block of FIG. 4a. There will now be stored in the random access memory the average offset obtained from aspirating a blank which is used in the remainder of the computations.

Once the blank has been aspirated, the actual value of standard 1 is entered on the numerical keyboard and A/C actuated. If two or three standards are to be used, they are then entered in sequence and the CC1 and CC2 keys actuated. It is necessary that the entries be made and the standards be aspirated in order of increasing concentration. The standards are then aspirated one at a time and the read button pushed. The indicator lamp above the read button will be lit until the measurement is completed whereupon the next measurement can be initiated by aspirating the next standard. As all this is occurring, the microprocessor is cycling through the program. As it goes through, the same path as described above will be followed until it reaches the decision block 125 of FIG. 4b. Now it will find that there is a numerical entry on the key data and will enter block 209 where it is instructed to append the digit to the entry register and display the entry. In other words, as the operator is entering it, the entered value will be displayed. In block 211, the instruction is given to set the numerical entry pending flag. The program then returns to start and will continue in this loop until there is no longer any key data numerical entries. At that point, the block 125 will be exited to block 217 and, if no error has been made in the entry and the clear entry button has not been pressed, decision block 129 will be entered. Since the numeric entry pending flag was set, this block will be exited to decision block 219 where the question is asked whether or not the A/C, CC1, CC2, EXP or ITIM key is on.

The computer, of course, is running through this loop quite rapidly and at this point, the operator will have entered the numerical data for the first concentration and have pressed the A/C button. The answer will thus be "yes" and block 215 will be entered causing the numerical entry to be stored. Block 217 will then be entered and the key A/C reset along with the numerical entry pending flag. The program then goes to G66 to FIG. 4c and thence to the decision block 139. Here, the answer will now be "no", i.e., that the key data is not AZ, and a decision block 219 will be entered asking whether the signal is CONC or EM. Since it is CONC, the answer will be "yes" and it will enter the decision block 221 where the question is asked whether the key data is A/C, CC1 or CC2. Since it is A/C, the answer is "yes" and the set read key flag block 141 is entered. Once again, the block 243 is entered which instructs a two second delay by reading 11 A/D data; the program then passes to decision block 245 which asks if the record is TC or ABS; as the answer is "no", it will enter block 145. Now the first sample concentrations are being measured and recorded. Once again, the blocks 145, 147, 149, 151 and 153 will be passed through and executed as described above which the blocks 155, 157 and 159 (FIG. 4d) will be passed through. Upon reaching block 161, the answer will be "no" and block 167 will be entered. The previously computed average offset will not be used to find concentration.

The program then goes to block 169 of FIG. 4e where concentration is computed as the value PKAV, i.e., the values obtained from the A-D's minus the average offset. The program continues and when block 173 is entered, the answer is "yes" and block 223 is entered. This directs finding of the expansion factor alpha to set the concentration equal to the A/C entry value. Alpha is then set equal to the A/C entry divided by the concentration as indicated in block 225. In other words, where only one calibration sample is entered, a slope for a linear relationship is computed. The A/C done flag is then set in block 226 and the program proceeds to block 175 where it sets DISP to the concentration times alpha.

Figure 4F:
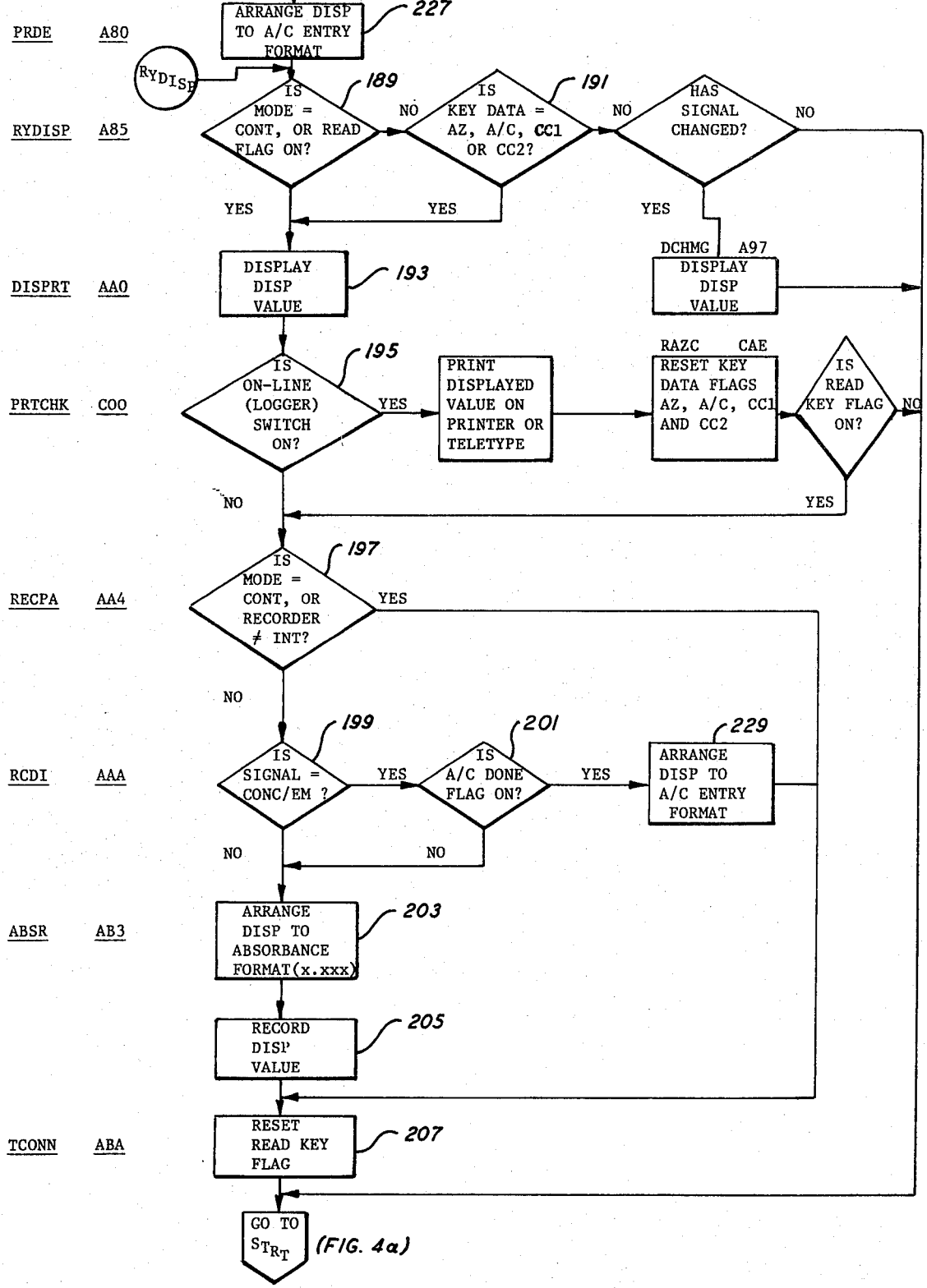

During this time, when the decision block 185 is reached, the A/C done flag will be on and the program will be directed to go to PRDE on FIG. 4f. Here, the instruction is given to block 227 to arrange the display to the A/C entry format. The other steps will occur as described above until the decision block 201 is reached where the answer will be "yes" and block 229 will cause DISP to be put in the A/C entry format. This value is then recorded as indicated by block 205, the read key flag reset, and the program goes back to start. Now, the first calibration data is stored.

The same steps described above will be followed in entering the numerical data associated with the second calibration sample and the program will proceed in the same manner until it reaches decision block 173 of FIG. 4e. Here, the answer will now be "no", and block 175 will cause the value DISP to be set equal to CONC times alpha. In block 177, the question is asked whether or not the key data is CC1. The answer to this will be "yes" and block 231 will be entered instructing that the values $\phi$, A/C entry, and the CC1 entry, be used as standards to find the curvature coefficients BCOF1 and CCOF1 after which the CC1 done flag is set by block 233. From this point, the block 235 is entered instructing that the CC1 curvature correction be applied to the value DISP whereafter, the program goes to PRDE of FIG. 4f. This portion of the program will be passed through in a manner described above with the DISP value displayed.

After going back to start, assuming a third sample has been used, its numerical data will be read in and, as the sample is aspirated, analog-to-digital converter data accumulated. The program will proceed in the manner described above until it reaches the decision block 177. Now, it will pass through that block to the decision block 179 where the answer will be "yes"; consequently, the program enters block 237 where it is given the instruction to use A/C, CC1, and CC2 entries as standards to find curvature correction coefficients BCOEF, CCOEF, and DCOEF, after which the CC2 done flag is set by block 239. Now the block 240 is entered indicating that the CC2 curvature correction is to be applied to DISP. Once again, the program goes to PRDE of FIG. 4f and after going through that section of the program in the manner described above, goes back to start. Now, the microcomputer has stored curvature correction constants based on two or three samples.

Measurements can now be made on an unknown sample. The program will proceed as described above through the blocks of FIG. 4a and will go through blocks 125, 127 and 129 of FIG. 4b; the answer in the lattermost block being "no", it will pass through blocks 131 and 133 going to decision block 135 of FIG. 4c from which it will exit to block 137. The answer here will be "yes" and the program will enter the block 139 and get an answer of "no". The answer in block 219 being "yes" and the answer in block 221 "no", it will then enter blockk 241 which asks whether the key data is "READ". The answer to this will be "yes" causing the program to enter the block 243 which instructs it to delay two seconds by reading 11 A/D data; it then passes to decision block 245 which asks whether the recorder is TC or ABS. As the answer to this is "no", it will go into block 145 and thence through blocks 147, 149, 151 and 153 in the manner described above; thereafter, it will again step through the blocks 155, 157, 159, 161 and 167 of FIG. 4d to reach block 169 of FIG. 4e. Here, the stored average offset will be subtracted from the measured value. Now the program will go to decision block 171 and get an answer "yes". At block 173, the answer will be "no" and DISP will be set equal to CONC times alpha. It will get a "no" answer in the decision blocks 177 and 179. However, on reaching block 181, it will receive an answer "yes" since the CC2 done flag is on. Thus, the block 240 will be entered and the instruction given to apply the CC2 curvature correction to DISP. This will be done and the program will go to PRDE. There, the steps described above will be carried out and the measured concentration displayed on the display 17 of FIG. 2.

The reminder of the instructions on the flow diagram relate to operating in different modes such as modes in which a continuous display is provided, i.e., setting the switch 37 to CONT, modes in which the signal switch 39 is set to absorbance, and modes in which peak height and peak area are measured, the latter being used particularly with graphite furnace atomizers. An examination of the flow diagrams will show that depending on which of these switches are set, slightly different procedures are followed. In addition, there are instructions associated with providing output data to a recorder or to a printer, all of which are executed in well known fashion.

Of particular interest in the various other modes of operation is the mode using the graphite furnace. In this mode of operation, the switch 37 will normally be set to peak height. This will cause the switch 46a and 46b of FIG. 3 to couple the log converter to the peak reader 49 and the peak reader 49 to the analog-to-digital converter 51. The peak reader will pick off the peak value measured during the integration cycle. In other words, instead of integrating over that whole period as is the case when operating with a flame, the peak reader 49 simply stores the peak value detected during that time.

In the program of FIGS. 4a–4f, the important difference to note is in decision block 151 (FIG. 4c) where the answer to the question regarding peak height will be "yes" causing the program to enter instruction block 251 where PKAV will set to the peak of the A/D data. A similar operation is carried out in blocks 157 and 253 of FIG. 4d. In other words, in this mode, instead of using the sum of the values obtained, the peak value is used. This directly relates to the characteristics of the graphite furnace in that the value of interest is the peak value. It will be noted that in essence, two peaks are being determined. The analog peak reader 49 determines the peak during each integration cycle with the microprocessor selecting out of all those peak values the highest peak value. This insures that if a fast peak is reached during an integration cycle, it will not be missed.

The key to the accuracy provided by the present invention is in the manner in which the computations shown on the flow diagram in blocks 231 and 237 (FIG. 4e) are made and are used to apply curvature corrections as shown in blocks 244 and 235. As noted above, the curvatue correction is based on the following equations:

2 standards:

$$CONC = \frac{K_1(ABS_i)}{K_2(ABS_i) - 1} \quad (1)$$

where: $i = 1, 2$, the sample number 3 standards:

$$CONC = \frac{K_1(ABS_i)^2 - K_3(ABS_i)}{K_2(ABS_i) - 1} \quad (2)$$

where: $i = 1, 2, 3$, the sample number

These equations are first used either in block 231 or 237 to find the coefficients noted in which the designations BCOF1 and CCOF1 relate to K1 and K2 in equation (1) and the coefficient BCOEF, CCOEF, DCOEF relate to the constants K1, K2, K3 of equation (2). If two known concentrations are used, then they are both substituted into equation (1) above and the two equations so obtained solved simultaneously to obtain K1 and K2. Where three known samples are used, the three known values along with their associated measured values are each substituted into equation (2) above and the three equations so obtained solved simultaneously to obtain K1, K2 and K3. Once these constants or coefficinets are determined, either equation (1) or (2) is used to compute concentration from absorbance by placing the measured absorbance value in the appropriate equation and carrying out the indicated multiplications and divisions by the constants so determined. Attached to this description and incorporated by this reference, is the program listing for carrying out this portion of the program. The program is an assembly listing with notations in English of the specific tasks being performed. It can be seen that it follows very closely the flow diagram but goes into additional detail, particularly with regard to the computations.

For the purpose of identification, the program listing is attached in the form of a zerographic copy of a computer print-out consisting of 16 sheets each headed "ASSEMBLY LISTING 12/16/74 1056 BANK 0 ROM 2" followed by a page number. The page numbers extend, continuously and inclusively, from 36-41, and additionally include pages 45 and 46. Each page spans two sheets and all sheets are marked with the attorney's docket number for this application, viz., ID-2190.

It will be evident to those skilled in the art that the steps carried out correspond to what is shown on the flow diagram and the computations necessary to solve equations (1) and (2) given above.

EXAMPLES

Tables I–VIII in FIGS. 5–15 show actual data obtained using the method and apparatus of the present invention. Tests have shown that it is possible to keep the error in most cases below 1%. This can be done if the lowest standard has a concentration no greater than 15 to 20% of the highest value. As a rule of thumb, standards can be chosen such that the first standard is at the end of the linear range for a particular element, the second concentration three times as great and a third concentration six times the maximum linear range concentration. Whether or not one, two, or three standards are used will depend to a large extent on the required accuracy and the range over which measurements are to be taken. If remaining with a linear range, an operation with one standard can be carried out. If accuracy is not as important or the range smaller, two rather than three standards can be used where a range of concentrations outside that which is linear.

What is claimed is:

1. In a photometric instrument in which radiant energy measurements are taken and used to determine a concentration, and in which the relationship between measured radiant energy values and concentration is non-linear over the full range desired to be measured, a method of correcting for the curvature which exists in the relationship comprising:
   (a) measuring the radiant energy with respect to at least two and not more than three samples of known concentration;
   (b) storing said known concentrations and their associated measured values;
   (c) determining in computing apparatus a number of constants equal to the number of samples which are such that, with two measured samples, the excess over one of a second constant times the measured value divided into a first constant times the measured value and, with three samples, said excess divided into a quantity equal to said first constant times the measured value squared minus a third constant times the measured value, for each sample, is equal to the known concentration;
   (d) storing said determined constants;
   (e) measuring such radiant energy with respect to an unknown sample and storing the measured value;
   (f) using the measured value of said unknown sample and said stored constants in said computing apparatus to determine the concentration of said unknown using the same relationship used to determine said constants; and
   (g) storing and displaying said unknown concentration.

2. The method according to claim 1 wherein said measured values reflect absorbance of the samples.

3. The method according to claim 1 wherein said measured values reflect emission of the samples.

4. The method according to claim 1 wherein said instrument is an atomic absorption spectrophotometer including means for providing an analog signal proportional to the intensity of light reaching the sample divided by the intensity of light transmitted through the sample, and further including the step of taking the log of said analog signal to obtain a log value and storing said log value as the value of absorbance.

5. The method according to claim 4 wherein said log value is an analog for and said method includes the further step of converting said log value to a digital value.

6. The method according to claim 5 further including the step of integrating said analog value over a predetermined cycle time.

7. The method according to claim 5 wherein said apparatus includes programmed digital computing means having a predetermined cycle time and receiving input data once during each cycle and said method further includes the step of measuring the peak value of said analog value during said cycle time.

8. In a photometric instrument in which radiant energy measurements are taken and used to determine a concentration, and in which the relationship between measured radiant energy values and concentration is non-linear over the full range desired to be measured, apparatus for correcting the curvature which exists in the relationship, comprising:
   (a) means for making radiant energy measurements;
   (b) computing means for
      (1) storing the known concentration values of two measured samples of known concentration and their associated measured radiant energy values;
      (2) determining two constants which are such that the excess over one of a second constant times the measured energy value divided into a first constant times the measured energy value, for each sample, is equal to the known concentration;

(3) storing the measured energy values of samples of unknown concentrations; and (4) using said measured energy values of unknown samples and said stored constants to determine the concentration of said unknown samples; and (c) means for storing and displaying said unknown concentration.

9. In a photometric instrument in which radiant energy measurements are taken and used to determine a concentration, and in which the relationship between measured radiant energy values and concentration is non-linear over the full range desired to be measured, apparatus for correcting the curvature which exists in the relationship, comprising:

(a) means for making radiant energy measurements;

(b) computing means for (1) storing the known concentration values of three measured samples of known concentration and their associated measured radiant energy values;

(2) determining three constants which are such that, the excess over one of a second constant times the measured energy value divided into a quantity equal to a first constant times the measured energy value squared minus a third constant times the measured energy value, for each sample, is equal to the known concentration;

(3) storing the measured energy values of samples of unknown concentrations; and (4) using said measured energy values of unknown samples and said stored constants to determine the concentration of said unknown samples; and (c) means for storing and displaying said unknown concentration.

10. In a photometric instrument in which radiant energy measurements are taken and used to determine a concentration, and in which the relationship between measured radiant energy values and concentration is non-linear over the full range desired to be measured, apparatus for correcting the curvature which exists in the relationship, comprising:

(a) means for making radiant energy measurements;

(b) computing means for (1) storing the known concentration values of at least two and not more than three measured samples of known concentration and their associated measured radiant energy values;

(2) determining a number of constants equal to the number of samples which are such that, with two measured samples, the excess over one of a second constant times the measured energy value divided into a first constant times the measured energy value and, with three samples, said excess divided into a quantity equal to said first constant times the measured energy value squared minus a third constant times the measured energy value, for each sample, is equal to the known concentration;

(3) storing the measured energy values of samples of unknown concentrations; and (4) using said measured energy values of unknown samples and said stored constants to determine the concentration of said unknown samples; and (c) means for storing and displaying said unknown concentration.

11. Apparatus according to claim 10 or claim 8 or claim 15 wherein said photometric instrument is an atomic absorption spectrophotometer and said measured energy values reflect absorbance.

12. Apparatus according to claim 10 or claim 8 or claim 9 wherein said instrument is an atomic absorption spectrophotometer including means for providing an analog signal proportional to the intensity of light reaching the sample divided by the intensity of light transmitted through the sample, and in which absorbance is equal to the log of this signal and further including a log converter for taking the log of said signal and means for storing said log as the value of absorbance in analog form.

13. Apparatus according to claim 12 wherein said computing means is digital computing means and further including an analog-to-digital converter for converting the output of said logrithmic converter to a digital value.

14. Apparatus according to claim 13 wherein said digital computing means has a predetermined cycle time and receives input data once during each cycle and further including means for integrating interposed between said log converter and said analog-to-digital converter for integrating the output of said log converter over said cycle time.

15. Apparatus according to claim 13 wherein said digital computing means has a predetermined cycle time and receives input data once during each cycle and further including means interposed between said log converter and said analog-to-digital converter for measuring the peak value of said log converter during said cycle time.

* * * * *

UNITED STATES PATENT AND TRADEMARK OFFICE
CERTIFICATE OF CORRECTION

PATENT NO. : 4,238,830

DATED : December 9, 1980

INVENTOR(S) : Hoshang A. Unvala

It is certified that error appears in the above-identified patent and that said Letters Patent are hereby corrected as shown below:

Column 14, line 20, change "15" to --9--.

Signed and Sealed this

Thirty-first Day of August 1982

[SEAL]

Attest:

GERALD J. MOSSINGHOFF

Attesting Officer

Commissioner of Patents and Trademarks